United States Patent [19]

Chu et al.

[11] Patent Number: 4,617,637
[45] Date of Patent: Oct. 14, 1986

[54] SERVO CONTROL SYSTEM FOR A RECIPROCATING PISTON RESPIRATOR

[75] Inventors: Raymond D. Chu, Boulder; Anthony C. Rubner, Arvada; Michael W. Fellinger, Boulder, all of Colo.

[73] Assignee: Lifecare Services, Inc., Boulder, Colo.

[21] Appl. No.: 753,275

[22] Filed: Jul. 9, 1985

[51] Int. Cl.$^4$ ............... G06F 15/20; F04B 35/04; A61M 16/00
[52] U.S. Cl. .................... 364/505; 364/510; 417/18; 417/415; 128/204.21; 128/205.18
[58] Field of Search ............ 364/506, 505, 164, 165, 364/175, 510; 417/18, 20, 22, 45, 415; 128/204.21, 204.22, 204.23, 205.18; 361/96; 328/142-144

[56] References Cited

U.S. PATENT DOCUMENTS

| | | | |
|---|---|---|---|
| 1,406,141 | 2/1922 | Anston | 128/205.18 |
| 4,108,574 | 8/1978 | Bartley et al. | 417/54 X |
| 4,197,576 | 4/1980 | Sánchez | 364/164 X |
| 4,215,681 | 8/1980 | Zalkin et al. | 128/205.18 X |
| 4,276,003 | 6/1981 | Perkins et al. | 417/415 |
| 4,277,832 | 7/1981 | Wong | 364/510 |
| 4,326,837 | 4/1982 | Gilson et al. | 417/415 X |
| 4,358,322 | 11/1982 | Sánchez | 364/164 X |
| 4,384,825 | 5/1983 | Thomas et al. | 417/22 |
| 4,425,805 | 1/1984 | Ogura et al. | 364/510 X |
| 4,432,063 | 2/1984 | Resnick | 364/175 X |
| 4,458,321 | 7/1984 | Whitney et al. | 364/165 X |
| 4,493,614 | 1/1985 | Chu et al. | 417/22 |
| 4,498,843 | 2/1985 | Schneider et al. | 417/22 |

FOREIGN PATENT DOCUMENTS 1541852 3/1979 United Kingdom ........... 417/22

OTHER PUBLICATIONS

Moore et al., "Improved Algorithm for Direct Digital Control", *Instruments and Control Systems*, Jan. 1970, pp. 70-74.
Jain et al., "A Control System for Long-Term Ventilation of the Lungs", *IEEE Transactions on Biomedical Engineering*, Jan. 1972, pp. 47-53.
Coles et al., "Computer Control of Respiration and Anaesthesia", *Medical and Biological Engineering*, May 1973, pp. 262-267.

*Primary Examiner*—Errol A. Krass
*Assistant Examiner*—Joseph L. Dixon
*Attorney, Agent, or Firm*—William W. Cochran, II

[57] ABSTRACT

A control system for moving a piston in a reciprocating piston respirator which utilizes predictive servo control techniques. Present invention uses nonlinear time domain analysis rather than linear frequency domain analysis to produce a predictive servo control system for precisely controlling the movement of a piston in a reciprocating piston respirator. A plurality of flow profiles can be produced using stored factor tables. Current pressure and position information are used in the predictive servo control system.

11 Claims, 7 Drawing Figures

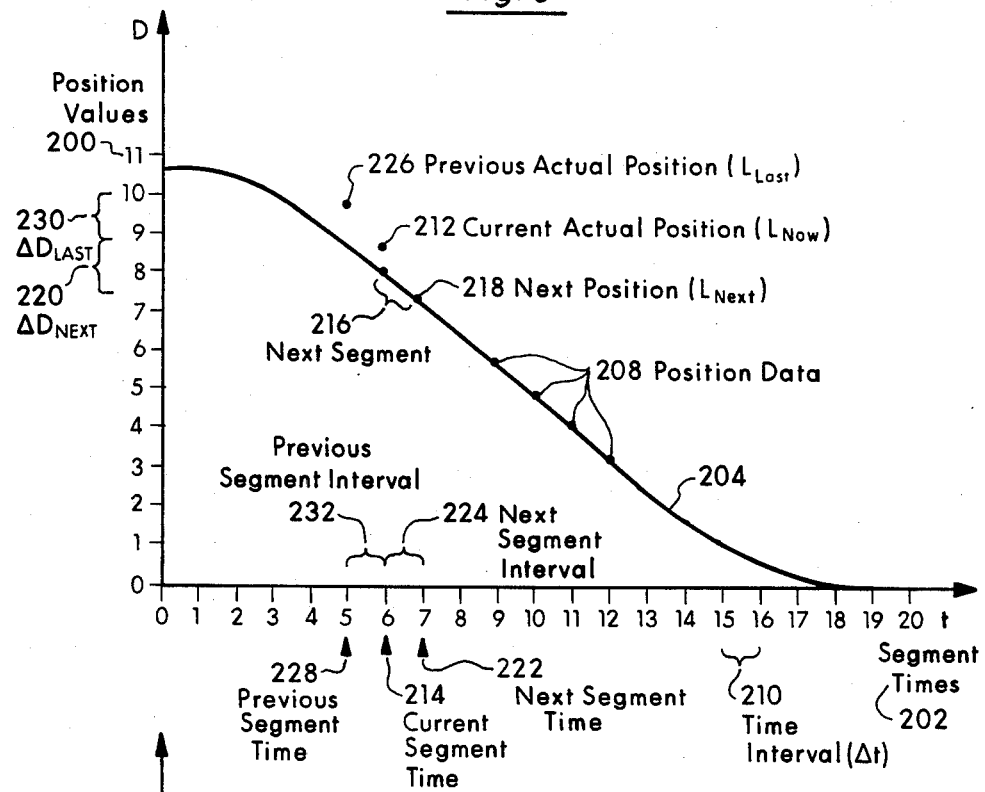
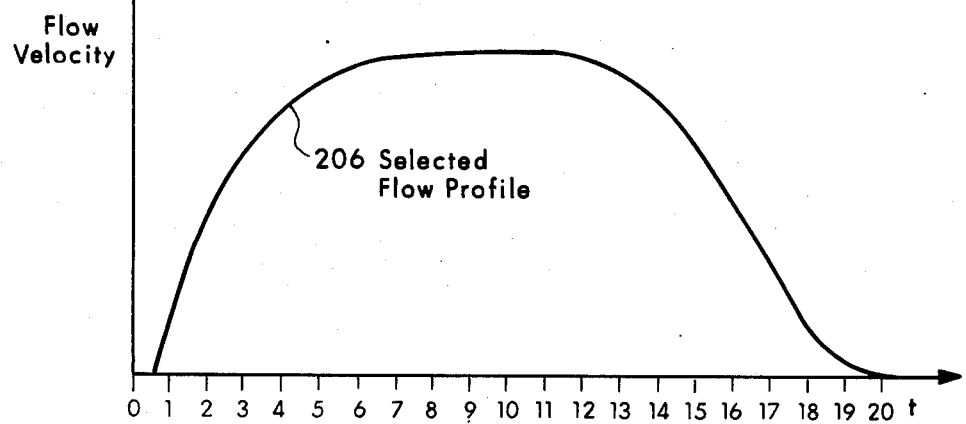

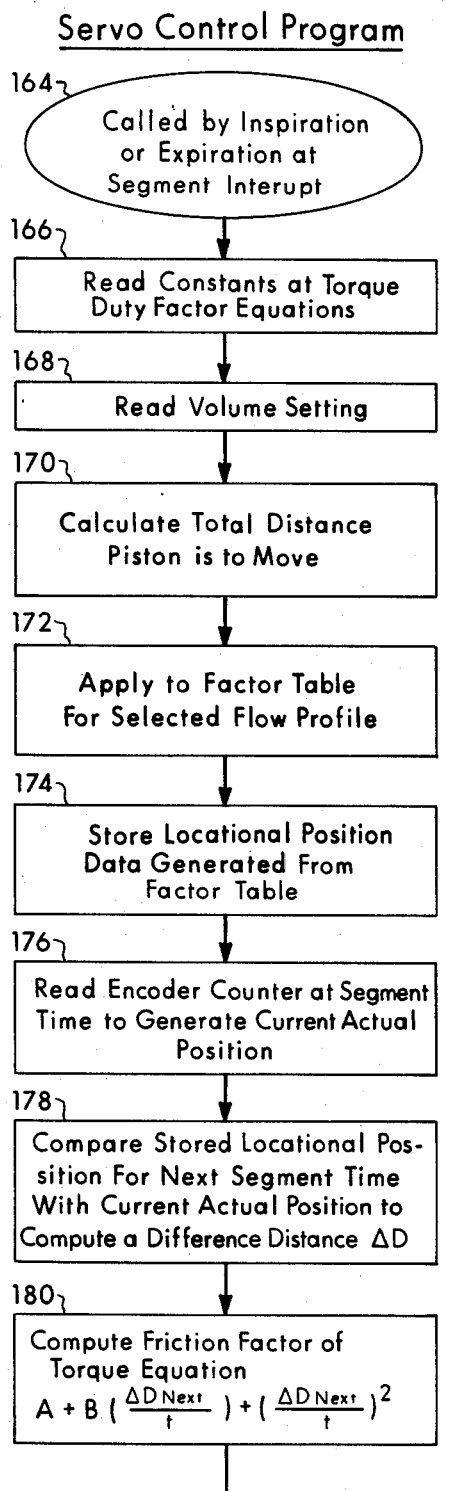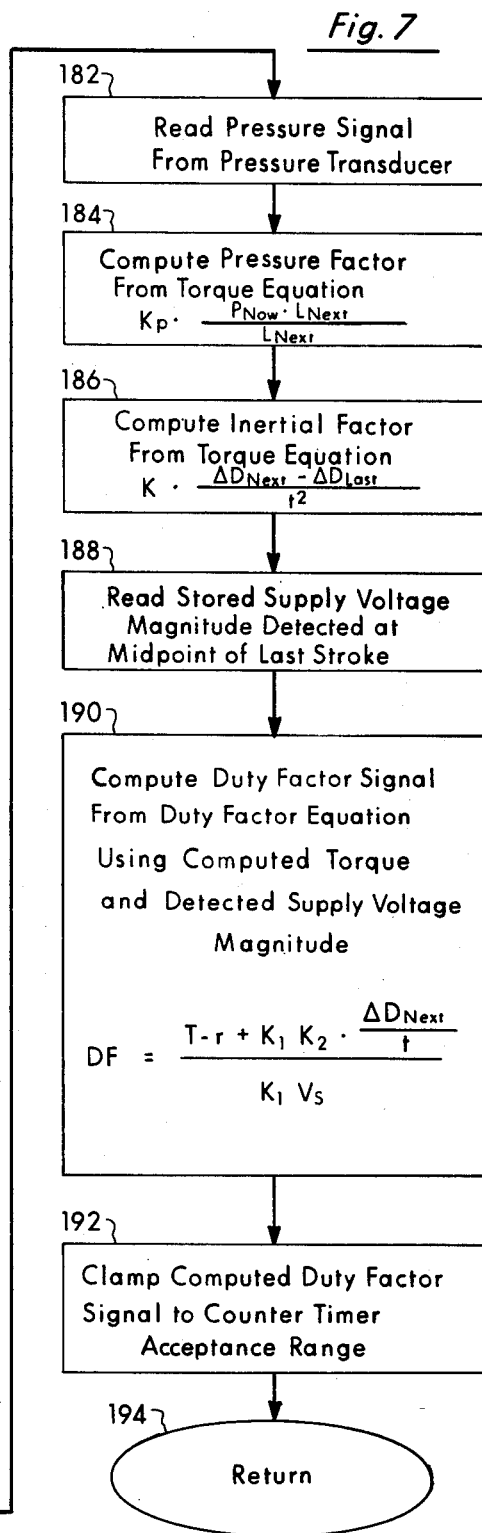
Fig. 7

4,617,637

SERVO CONTROL SYSTEM FOR A RECIPROCATING PISTON RESPIRATOR

BACKGROUND OF THE INVENTION

1. Field of the Invention

The present invention pertains generally to servo control systems and particularly to a servo control system for a reciprocating piston respirator.

2. Description of the Background

Within the past few years significant advancements have been made in reciprocating piston respirators. For example, U.S. Pat. No. 4,493,614 issued Jan. 15, 1985, to Chu et al, entitled "Pump for a Portable Ventilator" and assigned to Lifecare Services, Inc., Boulder, Color., discloses a piston cylinder arrangement in which a piston is reciprocally moved within the cylinder by a rotating shaft. A threaded shaft engages a threaded coupling device mounted in the piston so that linear movement is produced in the piston in response to the rotation of the threaded shaft. This linear relationship between the rotation of the motor in the movement of the piston comprises a basis for producing precise output flow characteristics from the reciprocating piston respirator. U.S. Pat. No. 4,493,514, cited above is specifically incorporated herein by reference for all that it discloses.

A patentability search was performed on this invention and the following U.S. Patents were uncovered.

| Inventor | U.S. Pat. No. | Issue Date |
| --- | --- | --- |
| McGuire | 3,610,782 | October 5, 1971 |
| Perkins et al | 4,276,003 | June 30, 1981 |
| Thomas et al | 4,384,825 | May 24, 1983 |
| Schneider et al | 4,498,843 | February 12, 1985 |

U.S. Pat. No. 4,384,825 issued May 24, 1983 to Thomas et al discloses a pump having a speed control circuit 16 which senses the motor speed of the pump drive motor 12 and provides an error signal to drive the motor 12 to maintain the pump speed constant.

U.S. Pat. No. 4,498,843 issued Feb. 12, 1985 to Schneider et al discloses a microprocessor 118 that senses the rotational speed of the pump output shaft using a optical encoding wheel and develops a driving voltage for electric motor 12.

U.S. Pat. No. 3,610,782 issued Oct. 5, 1971 to McGuire discloses a pump having a speed control servo which utilizes a variable pulse rate generator to vary the rate of the pump.

U.S. Pat. No. 4,276,003 issued June 30, 1981 to Perkins et al discloses a reciprocating piston pump wherein a reciprocating bearing mating with screw threads on the piston shaft cause the reciprocating piston to move. The motor control device 56 controls the movement of the piston.

Microprocessor control of the movement of a piston and a reciprocating piston pump has been specifically disclosed in the Schneider et al patent. Although such systems, such as disclosed in the Schneider et al patent are capable of controlling movement of a piston, such systems have been unable to precisely control the movement of the piston with a high degree of accuracy and simultaneously provide multiple output flow profiles. Conventional servo control methods employ classical control system analysis techniques which utilize linear feedback control methods to reduce error in the system. The classical techniques of control system analysis are disclosed in detail in "Elements of Control System Analysis; Classical and Modern Approaches" by Chih-Fan Chen and I. John Haas, Prentice Hall, Inc., New Jersey and "Automatic Control Systems" by Benjamin C. Kuo, 2nd Ed., Prentice Hall, Inc., New Jersey, both of which are specifically incorporated herein by reference for all that they disclose.

These classical techniques of control system analysis utilize frequency domain transformations of linear models which typically employ Laplace transformations. Although such classical linear analysis techiques are useful in servo control systems, such techniques are based upon reduction of an error signal from previous data. Consequently, such systems are based on "non-predictive" analysis techniques.

In order to implement conventional control system techniques, feedback systems are utilized which have inherent hysteresis to prevent undampened oscillations. The designed hysteresis of the system results in a built-in error factor at all times. The error factor greatly reduces the accuracy of the system.

Moreover, classical linear frequency domain control system analysis techniques rely upon detected velocity data as a basis for analysis and control. Instantaneous velocity signals in low velocity systems are extremely difficult to obtain. Low velocity tachometers for obtaining velocity information are extremely expensive and normally very inaccurate. The inaccuracy of such detection devices further adds to inaccuracies in the application of classical analysis techniques to low velocity servo systems.

Hence, classical techniques of servo control are unsuited for controlling the movement of the piston in a reciprocating piston respirator.

SUMMARY OF THE INVENTION

The present invention overcomes the disadvantages and limitations of the prior art by providing a system for generating predetermined flow characteristics in a reciprocating piston respirator by controlling movement of a piston comprising, a detector for generating a detected position signal indicative of a current actual position of the piston in the reciprocating piston respirator, an analysis device for using nonlinear predictive servo control techniques employing the detected position signal to generate a control system representative of a force sufficient to move the piston in the reciprocating piston respirator to a stored next position to produce the predetermined flow characteristics, and a device for generating the force sufficient to move the piston in the reciprocating respirator in response to the control signal.

The present invention may also comprise a method of generating predetermined flow characteristics in a reciprocating piston respirator comprising the steps of, generating position data indicative of a plurality of positions which a piston must assume in the reciprocating piston respirator at a plurality of successive substantially equally spaced segment times to produce the predetermined flow characteristics, detecting a current actual position of the piston at the plurality of successive substantially equally spaced time segments to produce actual position data, analyzing said position data and said actual position data using nonlinear, predictive servo control techniques by performing time domain analysis of frictional, pressure and inertial factors affecting movement of the piston to generate a control signal representative of a predicted force required to move the piston a difference distance (ΔD next) equal to the difference between the current actual position and a next position (L next) of the position data for each next segment, and generating the predicted force in response to the control signal.

The advantages of the present invention are that it utilizes nonlinear time domain predictive analysis techniques of servo control which provide a highly accurate method of controlling the relatively low velocity movement of the piston of the present invention in a reciprocating piston respirator. The present invention does not require the use of an expensive tachometer for deriving velocity information, but rather, employs a shaft encoder to derive position information for nonlinear time domain analysis. Locational position data is derived for a plurality of substantially equal segment times which describes the position which the piston must assume to produce the desired flow characteristics. Hence, the distance which the piston must move during each time interval is known in advance so that time required to move the piston can be predicted in advance. These predictive servo control techniques rely upon feed forward methods of control, rather than feedback methods of control used in classical servo control. Actual location positional data provided by the shaft encoder is sufficiently accurate to provide a precise method of generating data to utilize predictive servo control techniques.

BRIEF DESCRIPTION OF THE DRAWING

FIG. 3 is a graph of segment time vs. position values illustrating movement of the piston of the present invention.

FIG. 4 is a graph of flow velocity vs. segment times illustrating the flow profile produced by movement of the piston as illustrated in FIG. 3.

FIG. 7 is a schematic flow diagram illustrating the servo control program utilized in the flow diagram illustrated in FIG. 4.

DETAILED DESCRIPTION OF THE PRESENT INVENTION

Figure 1:
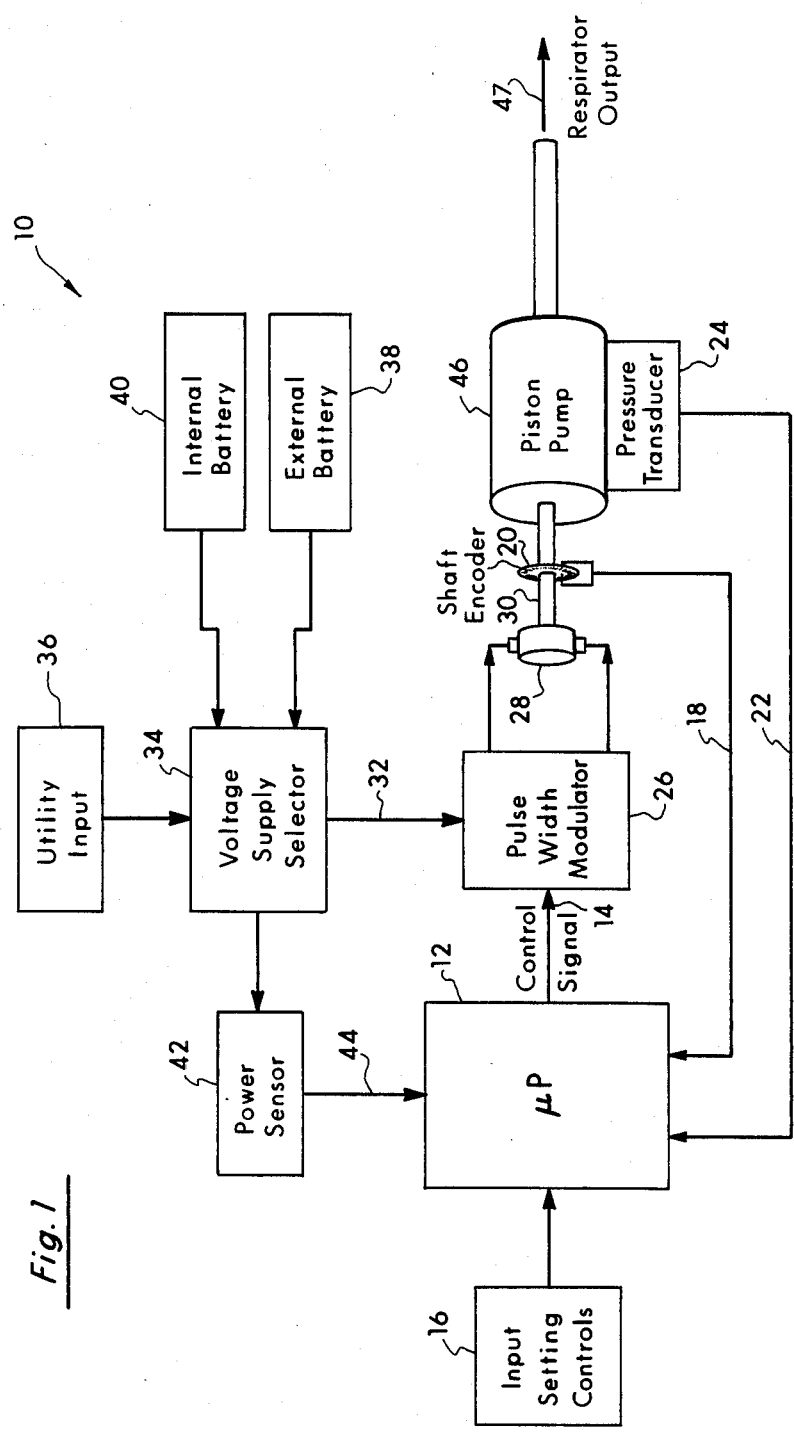
FIG. 1 is a schematic block diagram illustrating the system of the present invention.

FIG. 1 is a schematic block diagram of the control system 10 for the reciprocating piston respirator system of the present invention. The control system utilizes a microprocessor 12 which generates a control signal 14 in response to a predictive servo control algorithm which utilizes data from input setting controls 16, detected position signal 18 from shaft encoder 20 and pressure signal 22 from pressure transducer 24.

The signal produced by pulse-width modulator 26 has an average power corresponding to control signal input 14. The pulse-width modulated signal is applied to motor 28 which rotates a shaft 30 with a torque proportional to the average power of the pulse-width modulated signal. The reciprocating piston respirator can utilize a threaded shaft mounted in a piston in the manner disclosed in the above cited U.S. Pat. No. 4,493,614 which produces a linear movement of the piston in response to the rotational movement of the shaft 30.

Pulse-width modulator 26 pulse-width modulates a supply voltage 32 provided from a voltage supply selector 34. Voltage supply selector 34 selects either the utility input 36, internal battery input 38, or an external battery input 40 for use as supply voltage 32. The supply voltage 32 is monitored by power sensor 42 to detect the magnitude of the supply voltage during application of peak torque during each stroke of the piston pump 26. This provides an accurate measurement of the magnitude of the supply voltage. The power sensor signal 44 is applied to microprocessor 12 to adjust control signal 14 to provide the proper pulse-width modulation.

Microprocessor 12 may have one or more factor tables stored therein for generating position data to produce one or more preselected flow profiles. Torque and duty factor equations are also stored in the microprocssor 12 which utilizes frictional, pressure and inertial factors affecting movement of the piston in piston pump 46 for analysis using nonlinear time domain predictive servo control techniques.

Figure 2:
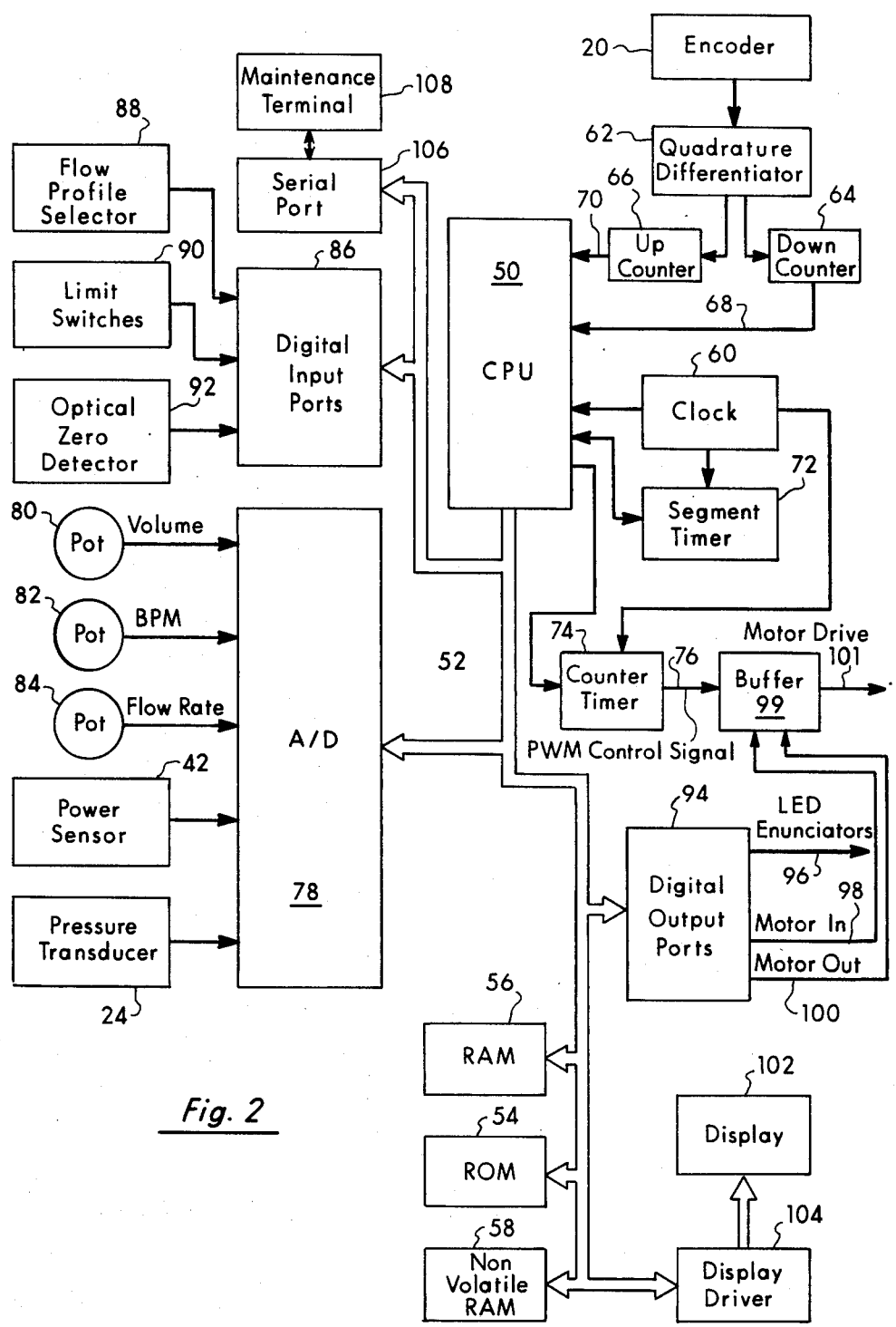
FIG. 2 is a schematic block diagram illustrating the microprocessor of the present invention.

FIG. 2 is a detailed block diagram of the microprocessor 12 and its associated devices. Microprocessor 12 uses a central processing unit 50 comprising an Intel 8085AH-1. The CPU is a complete 8 bit parallel central processing unit with a 0.65 microsecond instruction cycle. The memory system is coupled to CPU 50 through bus 52. The memory includes a read only memory 54, a read-write memory 56 and a non-volatile memory 58. Read only memory 54 consists of a number of binary information cells which are programmed outside of the device to contain program and data information. Read-write memory 56 consists of a number of binary information cells that, under program control, CPU 50 uses as a scratch pad for storing temporary data. Read-write memory 56 may be implemented using static or dynamic random access memory components. An Intel 2128 can be used which comprises a 16,384 bit static random access memory organized in 2,048 words by 8 bits. It employs fully static circuitry which eliminates the need for clocks, refresh, or address set and hold times. The auto power-down feature cuts power consumption when the device is disabled.

Non-volatile random access memory (RAM) 58 provides serial access static RAM access-ability and electronically erasable programmable read only memory (EEPROM) non-volatility. Device operation is primarily controlled through instructions which are clocked into the device as 16-bit words. The non-volatile memory provides semi-permanent storage of maintenance parameter settings. Extra storage can be used to report failures within the system for maintenance analysis. Clock 60 provides a clock pulse signal to bus 52 to control synchronous data transfers.

Encoder 20 provides a phase encoded signal which is differentiated by quadrature differentiator 62 which applies downcounts to downcounter 64 and upcounts to upcounter 66. Quadrature differentiator 62 comprises a standard phase comparitor device. Downcounter 64 and upcounter 66 can comprise Intel 8256 MURT timers which accumulate the up and down counts indicative of the position of the piston in the reciprocating piston respirator. The downcount signals 68 and upcount signal 70 are applied to CPU 50.

Clock 60 generates a clock signal which is applied to CPU 50 segment timer 72 and countertimer 74. Clock 60 provides timing to operate the system illustrated in FIG. 2. Segment timer 70 can comprise an Intel 8254 timer for producing segment time signals indicating the transition point between time intervals. Segment timer 72 is coupled to CPU 50 which computes the length of a segment interval. The length of the segment interval is loaded into segment timer 72. Segment timer 72 then provides a segment time signal indicating transition between time intervals. Countertimer 74 can also comprise an Intel 8254 programmable interval timer compatible for PWM drive which produces the pulse-width modulated control signal 76 which is proportional to the average voltage to be applied to the drive motor 28. A 5.12 megahertz signal is clocked into the countertimer 74 from system clock 60. A 20 kilohertz signal divided from system clock 60 acts as a gating signal for countertimer 74. Countertimer 74 is operated in a retriggerable one shot mode to produce a 20 kilohertz pulse-width modulated (PWM) signal for driving piston motor 28. Using 50 substantially equal segment intervals for each stroke, countertimer 74 is loaded by CPU 50 within an appropriate duty factor (DF) signal. The duty factor signal is computed by CPU 50 at each segment time regardless of the stroke length. The duty factor signal is derived from a torque equation based on information provided by encoder 20, parameters of the torque equation and detected parameter inputs through analog to digital converter (ADC) 78. Countertimer 74 initiates a countdown sequence from a predetermined number loaded by CPU 50 with the onset of each 20 kilohertz pulse, counting at the 5.12 megahertz rate provided by system clock 60. The pulse-width modulated control signal 76 produced by countertimer 74 is a 20 kilohertz pulse train with the width of each pulse directly proportional to the desired duty factor signal. This technique provides 255 different duty factor settings from full-off to full-on operation.

The torque equation stored in CPU 50 updates the torque required for the next segment of the total 50 segments throughout each stroke. The segment interval is computed for each designated stroke at the end of each breath when the piston returns to its home position. At this time, all control settings are updated and new piston equation parameters are calculated for the stroke. The new time interval for each stroke is loaded into segment timer 72. Segment timer 72 is clocked by an 80 kilohertz signal divided by input from system clock 60. Segment timer 72 then counts the prescribed time interval and provides an interrupt signal to CPU 50. The interrupt to CPU 50 invokes the torque equation at each segment time to update the duty factor signal applied to countertimer 74.

ADC 78 reads analog voltages from volume potentiometer 80, breath per minute potentiometer 82, flow rate potentiometer 84 power sensor 42 and pressure transducer 24. ADC 78 digitizes the input signals with information representative of the voltage level of the signal. The ADC is an integrated circuit device with an 8 channel multiplexer, an 8 bit analog to digital convertor and microprocessor compatible controlled logic. The 8 channel multiplexer can be controlled by a microprocessor through a three bit address decoder with addresses loaded to select any one of eight single ended analog signals connected directly to the comparator. The ADC uses successive approximation conversion techniques featuring a high impedance chopper stabilized comparator, a 256 end compensated voltage divider and a successive approximation register. The comparison and converting methods used in the ADC 78 eliminate the possibility for missing codes, non-monotonicity and the need for zero and full scale adjustment. Ratiometric conversion is provided by access to the reference voltage terminals.

Volume potentiometer 80 produces analog voltage indicative of the selected volume to be delivered. The breath per minute (BPM) potentiometer 82 generates an analog signal indicative of the selected breath per minute rate to be delivered by the reciprocating piston respirator. Flow rate potentiometer 84 produces an analog signal representative of the selected tidal flow rate (peak flow rate) to be delivered by the reciprocating piston respirator. The breath per minute input and flow rate input determine the inspiratory to expiratory ratio.

Power sensor 42 senses the voltage level of the power source during application of peak torque during the inspiratory stroke of the piston. Pressure transducer 24 provides a pressure signal at each segment time during the stroke. FIG. 1 discloses the three voltages which are sensed, i.e., utility input power, internal battery power and external battery power.

Pressure transducer 24 provides a highly sensitive reading of pressure applied to the piston at each segment time which is used in the torque equation to compute the pressure which will be applied against the piston during movement in the next segment. The converter 78 is coupled directly to bus 52 to transmit the digitzed data to CPU 50.

Digital input ports 86 provide high speed parallel data input from flow profile selector 88, limit switches 90 and optical zero detector 92. Flow profile selector 88 provides a digital input of the flow profile desired to be produced by the reciprocating respirator. The digital input can comprise a digital selector switch. Limit switches 90 are located within the reciprocating piston respirator cylinder to indicate movement of the piston beyond its limit points within the cylinder. The limit switches signal the CPU to stop movement of the piston immediately. Optical zero detector 92 produces an optical detector adjacent the bulkhead to precisely locate the piston adjacent the bulkhead. Optical zero detector 92 produces a zero reference input which provides a piston homing indicator at the end of each inhalation stroke. It assures an accurate piston reference position for the start of each breath.

Digital output ports 94 comprise parallel digital outputs which can be provided through peripheral interface adapters that are programmed for output. Digital output ports 94 can be used for high speed parallel data transmission or discreet output of any control compatible to binary format for switching external functions. CPU 50 produces LED enunciator outputs 96 which comprise six front panel LEDs and one internal LED. The LED indicators are controlled by the microprocessor through discreet latch registers. Motor-in signal 98 and motor-out signal 100 are also produced by digital output ports 94 to indicate the direction of the movement of the motor 28. Butter 99 receives the PWM control signal 76, motor-in signal 98 and motor-out signal 100 and produces a polarized electrical power signal which is substantially proportional to the output force necessary to drive the piston pump 46.

Display driver 102 and display 104 provide an LCD display of data produced by the central processing unit 50. Display driver 102 comprises a serial input LDC driver to drive LCD display 104. Data such as tidal volume, patient breath rate, inspiratory-expiratory ratio and other parameters of the system can be displayed on display 104.

Serial port 106 is coupled directly to bus 52. Bus 52 comprises a full duplex asynchronous receiver/transmitter. A programmable baud rate generator is included within serial port 106 to permit a variety of operating speeds without external components. Maintenance terminal 108 comprises a dumb type terminal which can be plugged into a board socket. Under friendly software communicates with the maintenance terminal 108 to establish parameters of the system.

FIG. 3 comprises a graph of distance of movement of the piston within piston pump 46 vs. time. FIG. 3 plots position values 200 versus segment times 202. Both the position values 200 and segment times 202 are arbitrary values as illustrated in FIG. 3. In accordance with the preferred embodiment, fifty separate segment times are utilized. Plot 204 indicates the positional values 200 which the piston must assume at the plurality of substantially equally spaced segment times 202 to produce the selected flow profile 206 illustrated in FIG. 4. A plurality of factor tables can be stored in microprocessor 12 to provide various positional values 200 to produce a plurality of selected flow profiles. Selected flow profile 206, illustrated in Figure, 4 comprises a commonly used sinusoidally shaped flow profile. The factor tables generate position data 208 which comprise curve 204. The plurality of substantially equally spaced segment times 202 are separated by a plurality of substantially equal time intervals 210. During operation, the piston may assume a current actual position ($L_{now}$) 212 at a current segment time 214. As can be seen from FIG. 3, the position value 200 of the current actual position 212 differs from the position data 208 at current segment time 214. The torque equation of the present invention determines the position value 200 of the position data 208 for next segment 216 which comprises the next position ($L_{next}$) 218. By looking ahead in a predictive manner, the torque equation can determine the difference distance ($\Delta D_{next}$) 220 which the piston must move to achieve the next position 218 at the next segment time 222. The difference distance ($\Delta D_{next}$) 220 must be moved by the piston during the next segment interval 224.

In a similar manner, a piston may have been at a previous actual position ($L_{last}$) 226 at a previous segment time 228. The torque equation then determines the previous difference distance ($\Delta D_{last}$) which the piston should have moved within the previous segment interval 232. Consequently, the torque equation determines the current actual position 212 of the piston at each current segment time 214 as it moves along curve 204 and compares the current actual position 212 with the next position 218 to prevent the torque required to move the piston the difference distance 220. FIG. 4 illustrates the selected flow profile 206 produced at the respirator output 47. When the piston assumes the positions indicated by position data 208, produced by the factor table, the selected flow profile 206 is produced as illustrated in FIG. 4.

Figure 5:
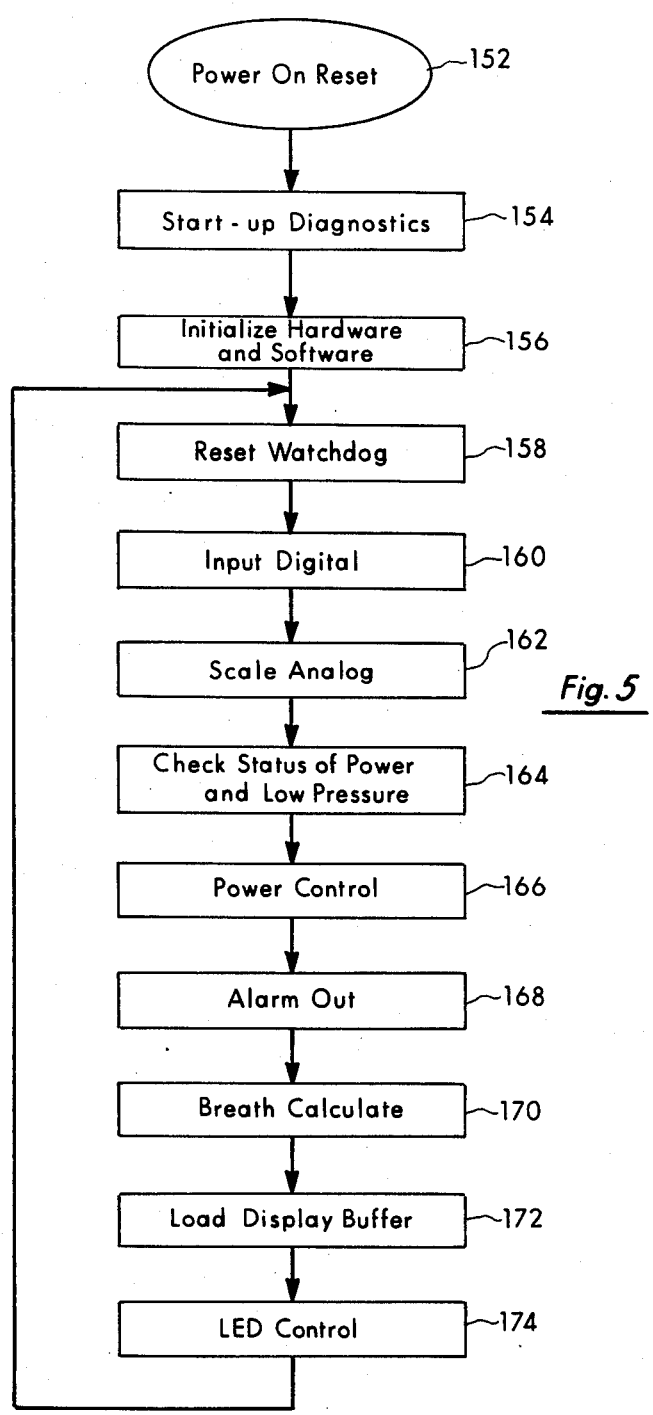
FIG. 5 is a schematic flow diagram illustrating the overall control program utilized in conjunction with the microprocessor.

FIG. 5 comprises a flow diagram of the microprocessor illustrated in FIG. 2. The power-on reset function 152 functions to reset the hardware. Start-up diagnostics 154 proceed through the diagnostic system and indicate to the operator the operational condition of the system. For example, each of the LED's is flashed to indicate that they are working. Additionally, the LCD display is operated to show its working condition. The initialized hardware and software step 156 functions to clear the registers so that the microprocessor can operate from a known state. The reset watch dog step 158 is a safety step for triggering operation of the microprocessor if it has gone into a stop or runaway mode. The input digital step 160 functions to read the flow profile selector 88, limit switches 90 and optical detector 92, as illustrated in FIG. 2. The scale analog step 162 sets-up ADC 78 to periodically read front panel potentiometers 80, 82, 84, power supple 42, pressure transducer 24. Analog inputs are read about ten times per second. The check status of power and low pressure step 162 checks the input power supply from the power sensor 42 and determines if the battery needs to be charged. The power control step 166 selects the source of power to be used by the system. Alarm out step 168 reveals the status of the entire system and determines if an alarm is necessary. Breath calculate step 170 reads the parameter inputs of the systems and performs arithmetic operations. Load display buffer 172 reads the operational values of the systems and feeds these values to the operator by way of display driver 102. LED control step 174 reviews the data base status and controls the LEDs to be lit. The program then recirculates to the reset watchdog and software step 158.

Figure 6:
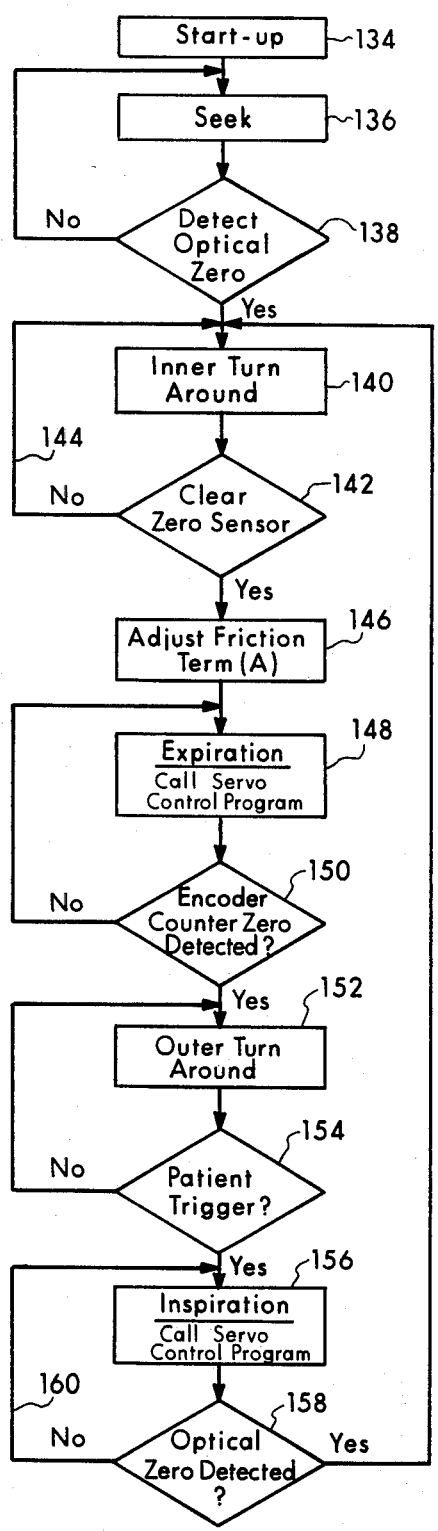
FIG. 6 is a schematic flow diagram illustrating the program utilized for controlling movement of the piston of the present invention.

The piston operation program is schematically illustrated in the flow chart disclosed in FIG. 6. The program begins with a start-up step 134 which initializes the program. The program then proceeds to a seek step 136 which moves the piston in a forward direction toward a bulkhead. Decision block 138 detects whenever the optical zero signal has been produced by optical zero detector 92. If the optical zero detector has not produced a signal, the program recirculates to the beginning of the seek step 136 to continue moving the piston. As soon as the optical zero mark is detected the program moves to the inner turn around step 140 which stops the drive motor 28 and produces a reverse torque in the motor to drive it away from the bulkhead. The program then proceeds to the cleared zero sensor decision step 142 to detect if optical zero detector 92 has ceased producing a signal to indicate that the piston has cleared the optical zero detector as a result of the application of reverse torque in the inner turn around step 140. If optical zero detector 92 is producing a signal, the program recirculates to inner turn around step 140, as indicated by feedback loop 144. As soon as the piston clears the zero point, the program proceeds to the adjust friction term step 146 which functions to adjust the "A" term of the torque equation based on the actual piston travel time last stroke, which is representative of the static friction of the system. The "A" term comprises the only free standing constant of the system and is adjusted at step 146 at the beginning of each stroke to compensate for differences in the predicted movement to the actual movement of the piston. The program then proceeds to the expiration cycle and calls the servo control program disclosed in FIG. 7. The program then proceeds to the encoder counter zero detected decision block 150 which detects if the shaft encoder of counter 166 has reached a full loaded value indicating that the piston has moved a predetermined programmed distance within the reciprocating piston respirator. The full volume to be delivered, which is selected on potentiometer 80, is loaded as a predetermined count in CPU 50. A comparison is made between the count in upcounter 66 and the predetermined loaded value to determine if the piston has moved the preselected distance to provide the preselected volume. When the proper number of encoder ticks is detected on upcounter 66, the program proceeds to outer turn around step 152 which stops the motor. The program then proceeds to the patient trigger decision box step 154 to determine if a patient trigger has been received to proceed with the movement of the piston. The patient trigger can be produced by an inspiratory effort by the patient or an automatic trigger provided by the system. If no trigger has been received, the piston remains in a stopped or paused position. As soon as the patient trigger is received the program proceeds to the inspiration step 156 which calls the servo control. Once the servo control program is completed the piston control program proceeds to decision block 158 to determine if the optical zero has been detected. If it has not, it recirculates to the inspiration step 156 by way of return loop 160. If the optical zero has been detected, the program then proceeds to the inner turn around step 140 by way of return loop 162.

FIG. 7 comprises a flow diagram of the servo control program. The servo control program is called by the inspiration or expiration step of the piston operation program at the segment interrupt time. The segment interrupt time is the segment time at which the end of a segment interval has been reached. Constants of the duty factor equation ae also read at this time. The torque equation is set forth below:

$$T = A + B(\Delta next/t) + C(\Delta D next/t)^2 + Kp + Kp(P_{now} + \Delta D_{next}) + Ka(\Delta D_{next} - \Delta D_{last})/\Delta t^2$$

where:
T = torque;
A = torque required to overcome static friction of said piston;
B = torque required to overcome friction of said piston (which is proportional to velocity of movement of said piston);
C = torque required to overcome friction of said piston which is proportional to velocity required of said piston;
$\Delta t$ = period of a single time interval;
Kp = pressure proportionality factor;
$L_{now}$ = current actual position of the piston;
$L_{next}$ = stored next position of said piston at a next segment time;
$L_{last}$ = previous actual position of said piston at a previous segment time;
$K_a$ = inertia factor of piston;
$\Delta D_{next}$ = the difference between position values for said next position ($L_{next}$) and said current actual position ($L_{now}$);
$P_{now}$ = measured pressure on said piston at $L_{now}$;
$\Delta D_{last}$ = the difference between position values for said current actual position ($L_{now}$) and said previous actual position ($L_{last}$).

The torque equation is an equation which predicts the torque required to move the piston the desired distance indicated by the position data using the current actual position of the piston and the current pressure. The piston data is the data generated by a factor table stored in the microprocessor which determines the position which the piston must assume in the cylinder to produce a selected flow profile. The torque equation, therefore, determines the torque required to move the piston across the next segment using predictive servo control techniques. As can be seen from the torque equation, it uses time domain analysis and comprises a nonlinear equation. It is based upon distance measurements rather than velocity measurements and pressure measurements resulting in the nonlinear nature of the equation. The duty factor equation uses the result of the torque equation to produce the duty factor necessary to produce the torque to drive the piston across the next segment. Each of the constants which are read into the microprocessor pertaining to the torque and duty factor equations are either derived empirically or calculated with the exception of the static friction term (A), which is adjusted during the course of each stroke. The duty factor equation is set forth below:

$$DF = (T \cdot r + K_1 K_2 \Delta D_{next}/\Delta t)/k_1 V_S$$

where: DF = duty factor
r = resistance of coils of said electric motor;
$K_1$ = proportionality factor relating torque produced by said electric motor to current supplied to said electric motor;
$K_2$ = proportionality factor relating back-emf of said electric motor and velocity of said piston;
$V_s$ = measured supply voltage;
$\Delta t$ = period of a single time interval.

Once the constants of the torque and duty factor equations are read into the microprocessor at step 166, the program proceeds to the read volume setting step 168 which reads the value of the potentiometer 80 indicating the select volume. The program then proceeds to step 170 to calculate the total distance the piston is to move in accordance with the volume setting.

The program then proceeds to step 172 to apply the factor table for the selected flow profile input from flow profile selector 88. The total distance the piston is moved is factored by the selected factor table to produce the position data indicating the positional values which the piston must assume in a predetermined number of substantially equal segment times to produce the selected flow profile.

The program then proceeds to step 174 to store the locational position data generated from the selected factor table. The encoder counters comprising upcounters 66 and downcounters 64 are then read by the program at the segment time to generate a current actual position ($L_{now}$) of the piston at step 176. The program then proceeds to step 178 to compare the stored next position ($L_{next}$) for the next segment time with the current actual position ($L_{now}$) to compute a difference distance signal ($\Delta D_{next}$). The program then computes a friction factor of the torque equation at step 180 to determine the frictional factors which affect the piston. The program then proceeds to step 182 to read the pressure signal from pressure transducer 24. This information is used in step 184 to compute the pressure factor from the torque equation. The inertial factor of the torque equation is then computed at step 186. The program then proceeds to step 188 to read the storage supply voltage magnitude detected at the midpoint of the last stroke, which is provided to the microprocessor by power sensor 42. This data is then used in step 190 together with the torque data and the resistance of the coils to compute the duty factor signal from the duty factor equation using computed torque and detected supply voltage magnitude. The program then proceeds to step 192 to clamp the computed duty factor signal to the counter time acceptance range. The program then proceeds to a return function at step 194.

The present invention therefore provides a control system for smoothly moving a piston in a reciprocating piston respirator using predictive servo control techniques which results in a very precise manner of controlling the movement of the piston. The present invention does not rely upon expensive and relatively inaccurate tachometers to produce velocity data, but rather, utilizes an inexpensive and accurate shaft encoder to produce locational position information. The present invention uses nonlinear time domain analysis rather than linear frequency domain analysis to produce a much more accurate model of the required movement of the piston to produce the selected flow profiles. As a result, the flow profiles generated by the device are considerably more precise than profiles which could be produced by a much more expensive device using linear frequency domain analysis.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to utilize the invention in various embodiments and various modifications as are suited to the particular use contemplated. It is intended that the appended claims be construed to include other alternative embodiments of the invention except insofar as limited by the prior art.

What is claimed is:

1. A system for generating predetermined flow characteristics in a reciprocating piston respirator by controlling movement of a piston comprising:

detector means for generating a detected position signal indicative of a current actual position of said piston in said reciprocating piston respirator;

analysis means for using nonlinear, predictive servo control techniques employing said detected position signal to generate a control signal representative of a force sufficient to move said piston in said reciprocating piston respirator to a stored next position to produce said predetermined flow characteristics comprising:

logic means for using said nonlinear, predictive servo control techniques for performing time domain analysis of fictional, pressure and inertial factors affecting movement of said piston to predict said force required to move said piston to said next position through the use of program control means for generating position data representative of a plurality of position values which said piston must assume at a plurality of substantially equally spaced segment times to produce said predetermined flow characteristics;

means for generating said force sufficient to move said piston in said reciprocating piston respirator in response to said control signal comprising:

pulse-width modulation means for producing a digital representation of a required power signal which is substantially proportional to said force;

direction selection means for producing a digital direction signal which substantially represents a direction of motor rotation;

buffer means for converting said digital representation of said required power signal and said digital direction signal into a polarized electrical power signal which is substantially proportional to said force;

motor means for converting said polarized electrical power signal into rotational power; and, piston displacement means for converting said rotational power into lateral movement of said piston.

2. A system for precisely controlling movement of a piston in a reciprocating piston respirator to produce a selected flow profile of a variable output flow from said respirator comprising:

motor means for inducing movement of said piston with a torque proportional to an average voltage applied to said motor means;

means for deriving position data representative of a plurality of successive next positions said piston must assume to produce said selected flow profile;

means for generating a plurality of successive detected position signals indicative of a plurality of successive current actual positions ($L_{now}$) of said piston at a plurality of successive current segment times;

means for successively comparing said detected position signals with said plurality of successive next positions to produce a plurality of difference distance signals;

means for generating a torque control signal (T) corresponding to said torque required to move said piston to said plurality of successive next positions in response to said difference distance signals;

pulse-width modulation means for pulse-width modulating a supply voltage in response to said torque control signal (T) to control said average voltage applied to said motor means.

3. The device of claim 2 wherein said means for generating a plurality of successive detected position signal ($L_{now}$) comprises:

encoder means for indicating said actual positions of said pistons.

4. The device of claim 3 wherein said means for generating a torque control signal comprises:

voltage sensor means for detecting a supply voltage magnitude during application of substantially maximum torque to produce a supply voltage signal ($V_s$);

pressure sensor means for sensing pressure on said piston at said plurality of successive current segment times to produce a plurality of successive current pressure signals ($P_{now}$);

logic means for storing detected data comprising said plurality of successive detected position signals, said supply voltage signal ($V_s$) and said plurality of successive current pressure signals ($P_{now}$), and for processing said detected data using nonlinear, predictive control system techniques to generate said torque control signal.

5. A method of precisely controlling movement of a piston in a reciprocating piston respirator by controlling the average power supplied to an electric motor used to drive said piston to produce a preselected flow profile comprising the steps of:

computing a plurality of position values of said piston at a plurality of segment times to produce said selected flow profile;

detecting an actual position value corresponding to a actual position of said piston at a current segment time;

determining a difference distance between said actual position value of said piston at each of said current segment times and said position value for a next segment time to produce a difference distance signal;

generating a torque control signal indicative of a torque required to move said piston said difference distance;

generating an average voltage to drive said electric motor with sufficient torque to move said piston said difference distance.

6. The method of claim 5 wherein said step of generating a torque control signal comprises the step of:

generating a friction factor signal by determining static friction factors, velocity friction factors and inertial friction factors affecting said piston during a next time interval between said current segment time and said next segment time.

7. The method of claim 6 wherein said step of generating a torque control signal comprises the step of:

generating a pressure factor signal by determining pressure factors during a next time interval between said current segment time and said next segment time from pressure readings taken at said current segment time.

8. The method of claim 7 wherein said step of generating a torque control signal comprises the steps of:

generating an inertia factor signal by determining acceleration during a next time interval between said current segment time and said next segment time from the difference between said difference distance and a previous difference distance corresponding to the difference between position values for a previous actual position and said current actual position.

9. The method of claim 5 wherein said step of generating a torque control signal comprises the step of:

generating a pressure factor signal by determining pressure factors during a next time interval between said current segment time and said next segment time from pressure readings taken at said current segment time.

10. The method of claim 5 wherein said step of generating a torque control signal comprises the step of:

generating an inertia factor signal by determining acceleration during a next time interval between said current segment time and said next segment time from the difference between said difference distance and a previous difference distance corresponding to the difference between position values for a previous actual position and said actual position.

11. The method of claim 5 wherein said step of generating a duty factor signal comprises:

sampling a supply voltage during application of substantially maximum torque to said piston to produce said measured supply voltage.

* * * * *